United States Patent [19]

Butter et al.

[11] 3,959,239

[45] May 25, 1976

[54] USE OF NICKEL CYCLOOCTADIENE AS A HYDROGENATION CATALYST

[75] Inventors: Stephen A. Butter, East Windsor; James G. Murray, East Brunswick, both of N.J.

[73] Assignee: Mobil Oil Corporation, New York, N.Y.

[22] Filed: May 5, 1975

[21] Appl. No.: 574,480

[52] U.S. Cl. .............................. 526/25; 260/690; 526/20; 526/90; 526/340; 526/347
[51] Int. Cl.² ........................................ C08C 19/02
[58] Field of Search ............ 260/85.1, 94.7 H, 96 H, 260/690; 450/613

[56] References Cited
UNITED STATES PATENTS

| | | | |
|---|---|---|---|
| 3,130,237 | 4/1964 | Wold | 260/94.7 H X |
| 3,432,518 | 3/1969 | Kallenback | 260/94.9 |
| 3,525,729 | 8/1970 | Gaeth | 260/94.3 |

*Primary Examiner*—William F. Hamrock
*Attorney, Agent, or Firm*—Charles A. Huggett; Howard M. Flournoy

[57] ABSTRACT

A process for the hydrogenation of hydrocarbon materials having olefinic unsaturation and/or olefinic-aromatic unsaturation, and particularly wherein hydrogenation is carried out at relatively low catalyst levels and mild reaction conditions whereby olefinic bonds are reduced and, when components of the reaction mixture contain aromatic unsaturation, to effect selective hydrogenation of olefinic bonds, without substantial, if any, hydrogenation of aromatic unsaturation; said process comprising contacting such hydrocarbon materials under hydrogenation reaction conditions of temperature and pressure in the presence of bis(1,5-cyclooctadiene) nickel as the hydrogenation catalyst.

8 Claims, No Drawings

USE OF NICKEL CYCLOOCTADIENE AS A HYDROGENATION CATALYST

BACKGROUND OF THE INVENTION

1. Field of the Invention

This invention relates to a hydrogenation process comprising the hydrogenation of hydrocarbon materials having olefinic or both olefinic and aromatic unsaturation wherein the olefinic bonds are reduced and when the reaction mixture contains compounds with aromatic unsaturation and/or compounds having both aromatic and olefinic unsaturation, selectively reducing the olefinic unsaturation of such compounds. Thus, this invention relates to the hydrogenation of α -and internally unsaturated olefins, e.g., such as octadecene-1 and octene-2 and polymeric materials such as copolymers of styrene and butadiene.

Accordingly, this invention more particularly relates to a hydrogenation process wherein such hydrocarbon materials are reacted with hydrogen in the presence of bis(1,5-cyclooctadiene) nickel as catalyst under mild hydrogenation conditions to selectively reduce olefinic bonds without hydrogenating, when present, aromatic unsaturation. In its most particular aspect, this invention is directed to a hydrogenation process wherein polymer materials, e.g., styrene/butadiene copolymers, containing both olefinic and aromatic unsaturation are hydrogenated under mild conditions (from about 400–500 psig and from about 50°–65°C.) in the presence of bis(1,5-cyclooctadiene) nickel as catalyst thereby reducing olefinic bonds of such copolymer without substantial, if any, reduction of their aromatic unsaturation.

2 Description of the Prior Art

The hydrogenation of olefins and olefinic polymers has previously been accomplished. The hydrogenation of olefinic polymers by complex iron, cobalt, nickel salts and alkyl lithium or alkyl aluminum components has been reported in the literature; see for example, J. C. Falk, J. Polymer Science (Part A-1) 9 2617 (1971) and U.S. Pat. No. 3,625,927 (1967).

Polymer hydrogenation has been accomplished, using for example, (1) an organonickel derivative, R Ni (where R= carboxylate or acetyacetone) and (2) an alkyl aluminum or lithium reducing agent. These prior systems, however, have deleterious effects due to extraneous metallic aluminum or lithium residues and possible contamination by carboxylate or acetylacetonatederived moieties in the polymer solution.

Furthermore, polymer hydrogenations in heterogeneous catalyst systems usually require high temperature, high pressure and high catalyst concentration. Under such conditions, the long reaction time may result in saturation of the aromatic rings of a reactant such as polystyrene block. In order to avoid such difficulties, the hereinbelow described catalyst system was developed.

DESCRIPTION OF THE INVENTION

Therefore, in accordance with this invention there is provided a hydrogenation process using a specific nickel catalyst under mild hydrogenation conditions, i.e. relatively low operating temperatures and pressures with fast rates of reaction, and high selectivity for olefinic (especially 1, 2 and 1, 4) unsaturation. The nickel catalyst, specifically bis(1,5-cyclooctadiene) nickel (0)[Ni(COD)₂], may be used at such low concentrations that its removal from a reaction mixture may not be required thereby simplifying the hydrogenation process by eliminating costly acid wash/drying steps used for conventional catalyst removal.

In an embodiment, a method is thus provided for hydrogenating hydrocarbon materials having both olefinic and aromatic unsaturation, or having α-and internal olefinic unsaturation or mixtures thereof, by reacting said hydrocarbons with hydrogen under mild hydrogenation conditions of temperature and pressure, in the presence of bis(1,5-cyclooctadiene) nickel as hydrogenation catalyst whereby the olefinic bonds of the hydrocarbon are reduced without substantial, if any, hydrogenation of aromatic unsaturation that may be present in components of the hydrogenation reaction mixture.

More particularly, a hydrogenation process is provided, using bis(1,5-cyclooctadiene) nickel as catalyst for the hydrogenation of styrene/butadiene copolymers. Ni(COD)₂ is generally highly active and stable under the mild hydrogenation conditions of this invention. However, minor amounts of a phosphine (e.g., triphenyl phosphine) may be utilized in the process to stabilize the Ni(COD)₂ if need be depending on variations in specific operating conditions used for the process.

The novel process of this invention is especially suitable for the hydrogenation of oil-soluble polymers such as may be prepared from diene-styrene or diene-alkylstyrene for example, styrene-butadiene copolymers. Such polymers are fully described in U.S. Pat. No. 3,867,295.

The aforenoted diene-styrene and diene-alkylstyrene copolymers possess desirable solubility in petroleum and other industrial fluids. Such dienes as for example butadiene, isoprene, 2,3-dimethylbutadiene, 2,3-diphenylbutadiene and others of the structure

wherein the dangling valences are substituted by hydrogen or alkyl or aryl groups of $C_1$ to $C_{10}$, and styrene or alkylstyrene provide suitable copolymers. Useful alkylstyrenes include propylstyrene, n-butylstyrene, i-butylstyrene, t-butylstyrene, n-amylstyrene, i-amylstyrene, hexylstyrenes, heptylstyrenes, methylpropylstyrene, methylbutylstyrene and the like. The butylstyrenes are most preferred. Mixtures of different alkylstyrenes or an alkylstyrene with styrene may also be used.

The butadiene-styrene system is representative of the above-referred to suitable copolymers. Units of butadiene and styrene in a typical oil soluble block may contain from about 5% to 60% styrene units based on the total number of units of butadiene and styrene; most preferably a block should contain between about 20% to 55% styrene units.

The following general procedure was used for preparation of bis(1,5-cyclooctadiene) nickel catalyst for the embodiments of the hydrogenation reactions set forth hereinafter.

A suitable reaction system is evacuated and filled with argon several times. Anhydrous nickel acetylacetonate Ni(AcAc)₂ is reacted with distilled 1,5-cycloocatdiene. The resultant suspension is cooled under argon to 0°C in an ice-water salt bath. Butadiene is then added to the reaction mixture in a heptane solution and triethylaluminum is added slowly over a 1 hour period. This mixture is stirred at 0–5°C. for about ½ hour. The product is recovered as yellow microcrystals and stored under argon.

Ni(COD)$_2$ has proven active for hydrogenation at levels of about 3 × 10$^{-4}$ moles catalyst per mole of the hydrocarbon material containing for example, olefinic unsaturation. The observed first-order rate in terms of time elapsed for 50% hydrogenation, t ½, varied between about 10–22 minutes at a Ni concentration of 2.1 × 10$^{-2}$ gram/gram polymer and about 31.5–50 minutes at 1.3 × 10$^{-2}$ g Ni/g of the styrene-butadiene copolymer (35 parts styrene/65 parts butadiene). These data illustrates that Ni(COD)$_2$ has high activity, at low concentration for olefinic hydrogenation.

In hydrogenations of octadecene-1, a model for 1,2-polymer unsaturation, Ni(COD)$_2$ catalyst levels of 4.4 × 10$^{-3}$, 2.1 × 10$^{-3}$, or 9 × 10$^{-4}$ g Ni/g octadecene-1 resulted in complete hydrogenation at one atmosphere in a few minutes time; in hydrogenations of octene-2, a model for 1,4 polymer unsaturation, Ni(COD)$_2$ concentration of 1% Ni/olefin also proceeded quantitavely.

To exemplify the practice of this invention styrenebutadiene (approx. 35/65 parts) copolymers are usually used in concentrations of from about 12–15% in benzene or cylcohexane (equivalent to approx. 0.012 moles copolymer per gram solution). Solutions may, if thought desirable, be diluted to about 3%. The Mn ~60,000 and Mw~88,000 gave an Mn/Mw ratio generally of about 1.5. Solution contaminants included small amounts of tetrahydrofuran (used as randomizing agent in the polymerization) and traces of acetic acid etc. The ratio of external (1,2) to internal (1,4) unsaturation in such copolymers was usually about 30/70.

In a typical 12% solution in cyclohexane and benzene, the styrene content of the copolymer was 30–35% with 70–65% butadiene, Mn ~60,000, Mw ~88,000 and Mw/Mn approximately 1.5; NMR analyses indicated that 29–32% of the unsaturation was 1,2 internal while 71–68% was of internal 1,4 unsaturation.

Three sources of unsaturation exist in the styrenebutadiene copolymer solution in benzene or toluene; the olefinic and aromatic unsaturation of the polymer and the aromatic unsaturation of the benzene or toluene solvent. The hydrogenation reaction conditions embodied by this invention have been found not to substantially, if at all, hydrogenate the styrenederived component of the copolymer or aromatic solvent.

Typically, styrene/butadiene copolymer hydrogenations were carried out at atmospheric pressure in a conventional setup with a mercury contained leveling bulb to maintain a hydrogen pressure of about 2.5 cm. The progress of reaction was monitored by following hydrogen absorption or by vapor phase chromatography. Higher pressure runs were conducted in a one-liter (or one gallon) stainless steel autoclave generally at 400–500 psig. The polymer hydrogenations were usually of 11–14% solutions in the autoclave runs or diluted to 3% in the atmospheric pressure apparatus.

Hyrogenation technique consisted of alternate evacuation and filling the unit with hydrogen several times before injecting the catalyst solution. The polymer solutions were stirred and heated to reaction temperature before adding catalyst in the atmopheric pressure apparatus; however, all components of the reaction solution were mixed before heating the sealed autoclave.

These process techniques are also useful for the reduction of alpha and internally unsaturated olefins, e.g., to octadiene 1 and octene-2, with Ni(COD)$_2$.

An i.r. (infrared) method was used for determining the degree of polymer hydrogenation. The 35% block of polystyrene common to the copolymer samples, was used as an internal standard to measure the amount of polydiene, e.g., butadiene unsaturation. The technique consisted of casting a polymer film on a salt plate drying for about 5 minutes at 100°C and determining the absorbence ratio of the 10.3µ/13.2µ bands in the infrared spectrum on a Perkins-Elmer 137 Infracord. The best results were obtained with a sample intensity giving a base line between about 0.05 and 0.10 with the strongest peaks not above about 0.05–0.06. A number of samples with various degrees of hydrogenation designated by iodine titration number and hydrogen absorption values were used to monitor hydrogenation activity and check hydrogen uptake values.

The activity of Ni(COD)$_2$ was evaluated under identical hydrogenation conditions, for example, with the prior art Ni-Al catalyst disclosed in U.S. Pat. No. 3,625,927. The catalytic procedure according to this invention provided a substantially more active catalyst [Ni(COD)$_2$]. AT lower catalyst levels, i.e. lower than about 2.1 × 10$^{-3}$ g Ni/g copolymer Ni(COD)$_2$ appeared to be more sensitive to impurity levels suggesting the need to stabilize the catalyst. However, this is usually not necessary unless the less reactive internal olefins are being hydrogenated. Without such stabilization Ni° metal slowly deposits (agglomerates) rendering the catalyst less active. With the more reactive α-olefin catalyst stabilization is unnecessary. The effect of utilizing triphenylphosphine with the Ni(COD)$_2$ is illustrated by the data in Table V.

One mole PPh$_3$/Ni completely inhibited catalytic activity. One-half mole PPh$_3$ (run 25) also drastically inhibited hydrogenation. Finally, 0.1:1 PPh$_3$/Ni (COD)$_2$, after 1.5 hour induction period, was sufficient to allow complete reduction of octene-2. Successful stabilization of the catalyst was thus achieved by the addition of minor amounts of phosphine, e.g., preferably from about 0.1:1.0 to about 0.1:0.5 mole of triphenylphosphine per mole of Ni(COD)$_2$.

The optimum reaction temperature using unstabilized Ni(COD)$_2$ is between about 50–65°C. At lower temperatures the hydrogenation is slower as COD is slowly reduced during formation of the active nickel (O) species. At temperatures above about 65°–70°C the rate of hydrogenation is also inhibited and the catalyst becomes deactivated presumably due to nickel (O) agglomeration with the formation of less active larger nickel crystallites.

Since little effect due to pressure was noted for runs at 400–500 psig or at atmospheric pressure, the influence of pressure is apparently substantially nil or zero.

Under the generally mild hydrogenation conditions practiced in this invention (about 50°–65°C, 1–500 psig and catalyst concentration of about 2.1 × 10$^{-3}$ g N./gi of copolymer), the Ni(COD)$_2$ catalyst has a high order of stability and requires substantially no stabilization.

The following Examples are intended to be merely illustrative and not to limit the scope of this invention in any manner.

EXAMPLE I

CATALYST PREPARATION

A three-necked 250 cc round-bottom flask was fitted with a 3-way stopcock for alternate argon-vacuum purge, a 50 cc pressure-equalized dropping funnel topped with a rubber serum stopper and a magnetic bar for stirring. The glassware was baked free of moisture evacuated and filled with argon several times since all operations had to be air and moisture free. Thirteen grams of anhydrous Ni(AcAc)$_2$ (dried at 110°C in a vacuum oven for several days) and 40 cc of freshly distilled toluene were added to the flask against a counterflow or argon. A freshly distilled sample of 1,5-cyclooctadiene (31.0 cc) was then added. The system was evacuated and filled with argon three more times. Under argon (entering via a blow-by bubbler) a resultant green suspension was cooled to 0°C in an ice-water salt bath. Butadiene (1.71 cc at −78°C) was condensed in a dry-ice cooled trap and added via a syringe needle through the serum stopper to the reaction mixture. A solution of triethylaluminum (24 grams, 34 cc of 24.2% concentration) in heptane was slowly added via the dropping funnel over a one hour period producing a brown-green mixture with yellow crystals. This mixture was then stirred at 0°–5°C for one half hour. A brown-yellow suspension which formed was warmed to room temperature and stirred for another two hours. Yellow crystals of Ni(COD)$_2$ were filtered anaerobically from the suspension in a Schlenk-tube apparatus under argon, sucked dry, and optionally washed with small portions of anhydrous ethyl ether (stored over LiAlH$_4$) and dried in vacuo ( 10$^{-2}$ torr for 17 hours). A yield of ca. 14 grams of yellow micro crystals of Ni(COD)$_2$ was obtained (100% of theory). Crystals were subsequently stored under argon in several small vials containing small rubber septa.

EXAMPLE II

A catalyst solution containing 0.095 grams of Ni(-COD)$_2$ in 10 cc toluene was added to one gram of styrene/butadiene (35/65 ) copolymer in 5.57 grams benzene and 20.6 cc toluene under hydrogen at 51°C. The solution was stirred for approximately three hours at 20 mm above atmospheric pressure with hydrogen being supplied as necessary. A total hydrogen absorption of 241.5 cc corresponding to 89.6% of theory was recorded. Neither solvent (toluene) nor styrene unsaturation was hydrogenated. Table I is a series of similar hydrogenations at approximately 1 atmosphere of pressure.

EXAMPLE III

The high-pressure hydrogenations, exemplified in runs 8–13, Table II, were carried out in the following manner, using run 11 as an example. A one-liter stainless steel autoclave was charged with four hundred grams of styrenebutadiene copolymer (12% solution in benzene), and 0.54 grams of Ni(COD)$_2$ dissolved in thirty cubic centimeters of benzene. The autoclave was evacuated and filled with hydrogen and pressurized to 500 psig at 20°C. Stirring was begun and the temperature gradually raised and held between 50° and 60°C for approximately seven hours while replenishing hydrogen. Approximately 365 psig was absorbed and the vessel was allowed to cool overnight. The pressure uptake and an infrared determination indicated that approximately 75% of the olefinic bonds had been hydrogenated. An analytical determination for the concentration of cyclohexane in the product mixture revealed 0.8% cyclohexane indicating that less than one percent of the benzene solvent was hydrogenated.

EXAMPLE IV

Under conditions equivalent to those of Example II a corresponding concentration (based on % Ni) of Ni(A-cAc)$_2$ 3 Et$_3$Al, a well known hydrogenation catalyst prepared in accordance with conventional procedures, an analogous hydrogenation was carried out.

The half-life for hydrogenation (time elapsed for 50% reaction) using Ni(COD)$_2$ was 10 minutes compared with 16 minutes using Ni(AcAc) $_2$3 Et$_3$Al. Therefore, Ni(COD)$_2$ is 60% more active than this prior art system. In addition, the activity of Ni(AcAc)$_2$ Et$_3$Al decreased with time while Ni(COD)$_2$ appeared considerably more stable with respect to decline in activity. See Table III.

Additionally, the activity of Ni(COD)$_2$ was thus otherwise comparable to Nickel acetylacetonate triethylaluminum acetylacetonate-derived moieties.

EXAMPLE V

The atmospheric pressure hydrogenation unit of Example II used in reducing the styrene/butadiene copolymer was used to hydrogenate the pure olefins of Tables IV and V. The unit contained a 100 cc. burette and mercury-filled leveling bulb and was capable of holding approximately 0.003–0.004 moles of hydrogen per filling. Using run 21 Table IV, as an example, a 250 cc glass flask was charged with 6.0547 grams of octadecene-1 (previously percolated through alumina under an argon atmosphere) and 50.0 cubic centimeters of toluene.

The flask was attached to the hydrogenation unit and evacuated and filled with hydrogen several times, then heated to 53°C while being magnetically stirred. A solution containing 0.0275 grams of Ni(COD)$_2$ in 4.0 cubic centimeters of toluene was rapidly injected via syringe into the olefin solution. Hydrogen was added as necessary to maintain a pressure approximately two centimeters above atmospheric, while the temperature was held at 55°C. After 190 minutes during which time 483 cc. of hydrogen were absorbed (corresponding to 97% of theory) the reaction mixture was cooled and analyzed. The infrared spectrum indicated virtually complete hydrogenation of octadecene-1 had occurred. This was verified by vapor phase chomatographic analysis which showed the presence of octadecene, and absence of the olefin.

The results of the Examples and the data disclosed throughout the specification hereinabove and Tables I - V illustrate the fact that Ni)COD)$_2$ is a highly active catalyst for reductions under mild conditions, that it can be used in concentrations low enough that its removal from a reaction mixture would not be required thus simplifying hydrogenation processes, that its use avoids contamination by the residues which are formed using the conventional zerovalent nickel complex catalysts of the prior art (e.g., Ni-Al) and that the reduction of aromatics (solvents or otherwise) in the reaction mixture is virtually eliminated. The costly acid wash and drying steps use for catalyst removal may therefore be eleiminated and the catalyst of this invention may be used in the presence of functional groups labile to the reducing agent of the conventional prior art zerovalent nickel catalyst.

TABLE I

HYDROGENATION OF STYRENE-BUTADIENE COPOLYMER
(3% IN BENZENE/TOLUENE SOLUTION)
APPROX. 1 ATM. PRESSURE
CATALYST: Ni (COD)$_2$

| Run No. | % be weight Ni/Polymer | % Hydro-genation | Temp. °C. | '1/2* |
|---|---|---|---|---|
| 1 | 2.1 | 90 | 56 | 10 min. |
| 2 | 2.1 | 50 | 53 | 22 |
| 3 | 2.1 | 75 | 54 | 15 |
| 4 | 2.1 | 57 | 66 | 19 |
| 5 | ~0.85 | >65 | 65 | ~300 (cyclohexane) |
| 6 | 1.3 | 59 | 56 | 31.5 |
| 7 | 1.3 | 25–48 | 54 | 50 |

*'1/2 refers to kinetic half-life in this and succeeding tables

TABLE II

HYDROGENATION OF STYRENE-BUTADIENE COPOLYMER
(12% SOLUTION) APPROX. 500 psig
CATALYST: Ni(COD)$_2$, SOLVENT BENZENE

| Run No. | % By Weight Ni Polymer | % Hydro-genation | Temp. °C. | '1/2 |
|---|---|---|---|---|
| 8 | 0.052 | 25 | 60 | 800 min. |
| 9 | 0.14 | 50 | ~52 | 220 |
| 10 | 0.15 | 55 | 62 | 200 |
| 11 | 0.18 | 75 | 50–60 | 80 |
| 12 | 0.18 | 45–55 | 85, | 170 (cyclohexane) |
| 13 | 0.08 | ~0 | 50, | - (+BuLi) |

TABLE III

HYDROGENATION OF SB COPOLYMER
(3% SOLUTION) WITH Ni(AcAc)
Et$_3$Al APPROX. 1 ATM.

| Run No. | % By Weight Ni/Polymer | % Hydro-genation | Temp. °C. | '1/2 |
|---|---|---|---|---|
| 14 | 0.57 | 83 | 67 | 43 min. (cyclohexane) |
| 15 | 2.1 | 95 | 56 | 16 (bz-toluene) |
| 16 | 1.3 | 92 | 54 | 12.5 (bz-toluene) |
| 17 | 0.57 | 5 | 65 | -cyclohexane* |
| 18 | 0.57 | 52 | 65 | -14% in cyclohexane* |

*Poor catalyst preparations

TABLE IV

HYDROGENATION OF 1-OCTADECENE
(11% SOLUTION) WITH Ni(COD)$_2$
APPROX. 1 ATMOSPHERE
TOLUENE SOLVENT

| Run No. | % by weight Ni/Olefin | % Hydrogenation | Temp.°C. | '1/2 |
|---|---|---|---|---|
| 19 | 0.44 | 100 | 55 | <4 min |
| 20 | 0.21 | >95 | 54 | <4 min |
| 21 | 0.09 | >95 | 54 | <4 min |

TABLE V

HYDROGENATION OF 2-OCTENE
(7% SOLUTION) WITH Ni(COD)$_2$
AT APPROX. 1 ATMOSPHERE
TOLUENE SOLVENT 55°C

| Run No. | % By Weight Ni/Olefin | Ph$_3$ P/Ni | % Hydro-genation | '1/2, min. |
|---|---|---|---|---|
| 22 | 1.0 | 0 | >95 | 21 |
| 23 | 0.3 | 0 | 40 | 63 |
| 24 | 0.3 | 1:1 | 0 | ∞ |
| 25 | 0.3 | 0.5:1 | 8–10 | 2–2.5 × 10$^3$ |
| 26 | 0.3 | 0.1:1 | >98 | 73 (90 min. induction period) |

Furthermore the rate of reaction using this process proceeds at a rapid, linear rate, reducing reaction time and allowing hydrogenation to reach substantial completeness in relatively shorter period of time.

This invention, illustrated by the specific examples, is described in such a manner as to include obvious variations and modifications apparent to one of ordinary skill in the art.

What is claimed is:

1. A process for hydrogenating hydrocarbon materials having olefinic unsaturation and/or olefinic-aromatic unsaturation whereby olefinic bonds are reduced and when components of the reaction mixture contain aromatic unsaturation selective hydrogenation of olefinic bonds is effected without substantial, if any, hydrogenation of aromatic unsaturation; said process comprising contacting such hydrocarbon materials under hydrogenation reaction conditions of temperature and pressure in the presence of bis (1,5-cyclooctadiene) nickel as hydrogenation catalyst.

2. The process of claim 1 wherein the hydrocarbon material is a copolymer derived from styrene and butadiene.

3. The process of claim 2 wherein that portion of the copolymer attributable to butadiene is reduced while that portion attributable to styrene is substantially unhydrogenated.

4. The process of claim 1 wherein the hydrocarbon material has alpha- or internal-olefinic unsaturation.

5. The process of claim 1 wherein the reaction temperature is from about 50° to about 65°C and the pressure is from about atmospheric to about 500 psig.

6. The process of claim 5 wherein the reaction temperature is from about 55°–60°C and the pressure is about 400 psig.

7. The process of claim 1 wherein the nickel catalyst is stabilized by minor amounts of triphenyl phosphine.

8. The process of claim 7 wherein the nickel catalyst is stabilized by from about 0.1:1–0.1:0.5 mole of phosphine per mole of catalyst.

* * * * *